US00PP35650P2

(12) United States Plant Patent
Barba

(10) Patent No.: US PP35,650 P2
(45) Date of Patent: Feb. 13, 2024

(54) GRAPEVINE PLANT DENOMINATED 'INIA-G4'

(50) Latin Name: ***Vitis vinifera* L.**
Varietal Denomination: INIA-G4

(71) Applicant: Instituto de Investigaciones Agropecuarias, Santiago (CL)

(72) Inventor: Paola Barba, Santiago (CL)

(73) Assignee: INSTITUTO DE INVESTIGACIONES AGROPECUARIAS, Santiago (CL)

( * ) Notice: Subject to any disclaimer, the term of this patent is extended or adjusted under 35 U.S.C. 154(b) by 0 days.

(21) Appl. No.: 18/111,062

(22) Filed: Feb. 17, 2023

(51) Int. Cl.
*A01H 5/08* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./207
CPC ..... A01H 6/88; A01H 5/08
See application file for complete search history.

*Primary Examiner* — Keith O. Robinson
(74) *Attorney, Agent, or Firm* — Greer, Burns & Crain, Ltd

(57) ABSTRACT

A new and distinct grapevine variety denominated 'INIA-G4'. The new grapevine is characterized by producing ovoid green yellowish berries, with firm texture, small seed traces and early midseason ripening. Vines are vigorous and highly productive. The clusters are abundant on the vine, large in size and naturally loose, with good keeping and shipping quality.

12 Drawing Sheets

Latin name: *Vitis vinifera* L.
Varietal denomination: INIA-G4.

BACKGROUND

The present invention relates to the discovery and asexual propagation of a new variety of grapevine, *Vitis vinifera* L. denominated INIA-G4. This new cultivar resulted from controlled hybridization between selection 23 ('Ruby Seedless' (unpatented) x 'Centennial Seedless' (patent 4784, expired)) (♀) and 'Sugraone' (♂) (patent 3106, expired) performed in Santiago, Chile (latitude 33°34°22"S 70°37'31"W), corroborated by molecular markers techniques. Plants were produced from maternal parent selection 23 from embryo rescue. The original vine was planted in in Santiago, Chile and further propagated from dormant shoot tips which are straight hardwood cuttings for its agronomical evaluation.

SUMMARY

INIA-G4' produces firm, ovoid, green-yellow and sweet berries. Berries are large in size reaching about 4.0 g. Berry size can be increased with application of gibberellic acid. Berries are mostly seedless, but on occasions could develop rudimentary soft seed traces of large size. The clusters are abundant in the vine, large in size, conical and loose in density, with about 483 g. With agronomical practices clusters reach about 700 g. The fruit has export quality attributes and good storage and shipping characteristics. Vines are vigorous and present high bud fruitfulness at the basal buds, therefore spur pruning may be used to obtain high yields.

'INIA-G4' presents green-yellow berries, while berries from its maternal parent, selection 23, are pink. 'INIA-G4' is different from its paternal parent 'Sugraone' by having rudimentary seeds instead of seedlessness and by later maturity time. The new variety also has a better shipping and storage quality. 'INIA-G4' is similar to 'Thompson Seedless' (unpatented) in color and maturity time although firmer berries. INIA-G4 differs from this cultivar for having bigger and looser clusters and higher bud fertility and productivity. The new 'INIA-G4' variety has shown to maintain its distinguishing characteristics through successive asexual propagation by from straight hardwood cuttings in Santiago, Chile. Plants of INIA-G4 tolerate Mediterranean winter cold by dormancy mechanisms, but no tests have been conducted to set specific winter thresholds. Water needs during growing season are related to plant vigor and climate demand, but irrigation is always required for fruit quality.

Fruit has average shipping qualities; with average resistance to insects and diseases similar to other *Vitis vinifera* cvs. Powdery Mildew (*Uncinola necator*) and Grey Mold (*Botrytis cinerea*) are the main diseases that could affect the fruit and need to be controlled with common practices, like fungicide sprays and canopy management.

BRIEF DESCRIPTION OF THE FIGURES

The drawings of the grapevine of the present invention are color photographs as follows:

FIG. 7B is a picture of a berry being cut through, and

DETALIED BOTANICAL DESCRIPTION

Figure 1:
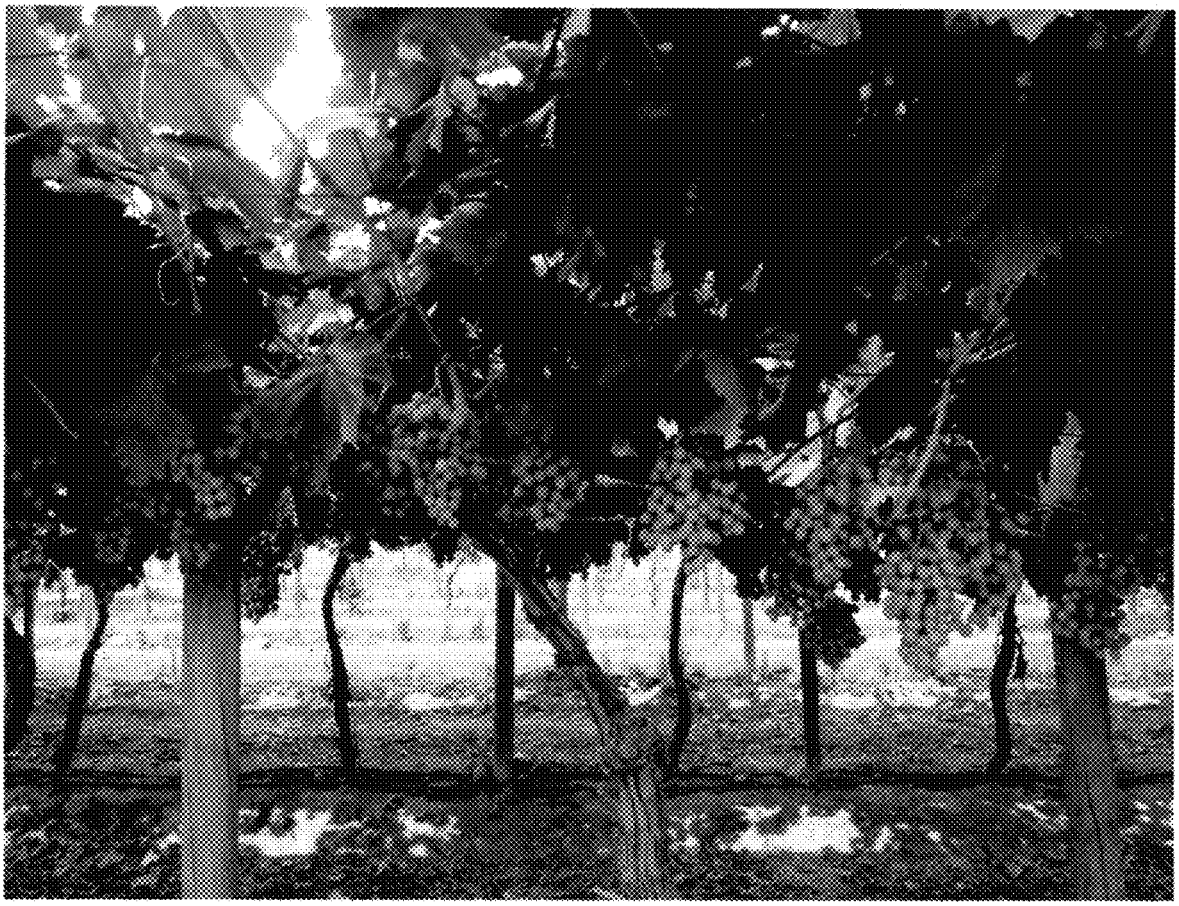
FIG. 1 is a picture of a mature four-year old plant.
Figure 2A:
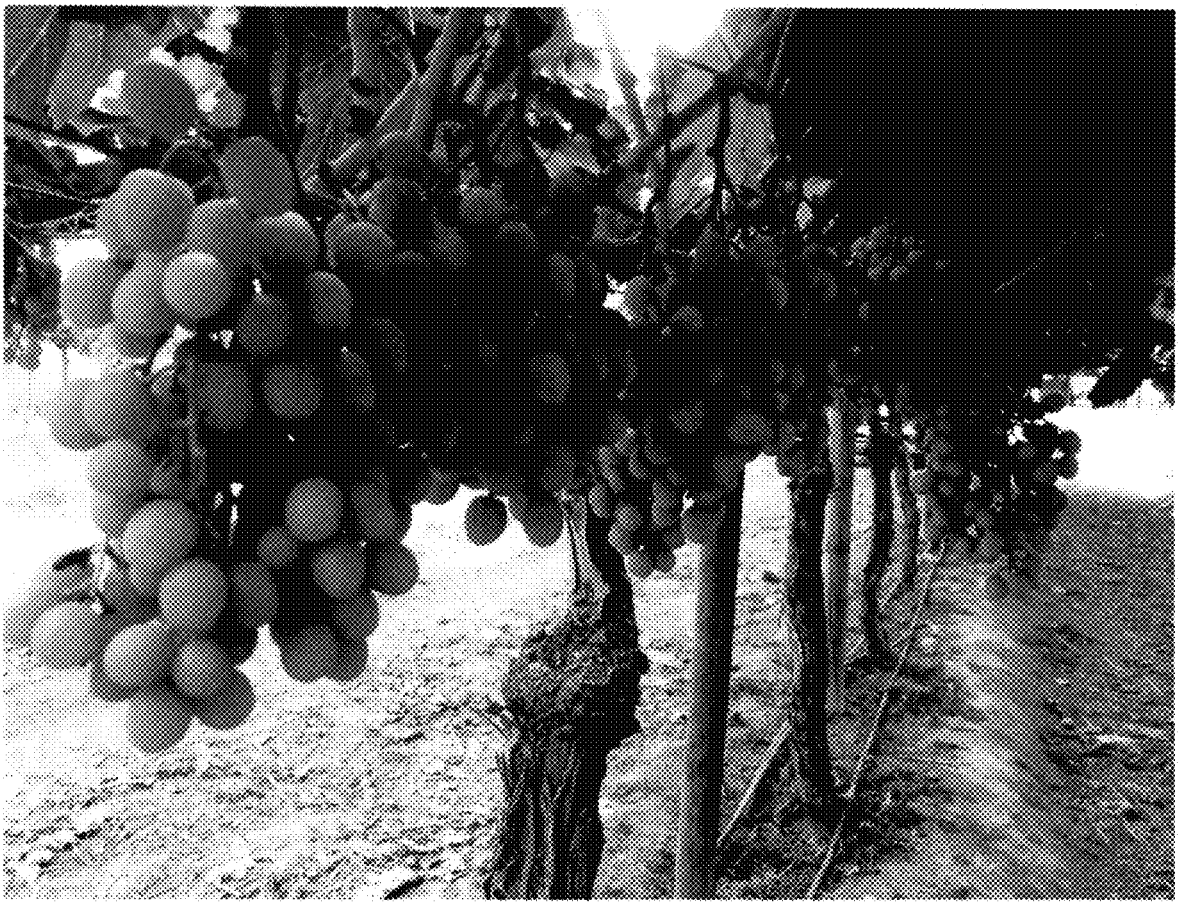
FIG. 2A is a picture of mature commercially handled clusters on vine.
Figure 2B:
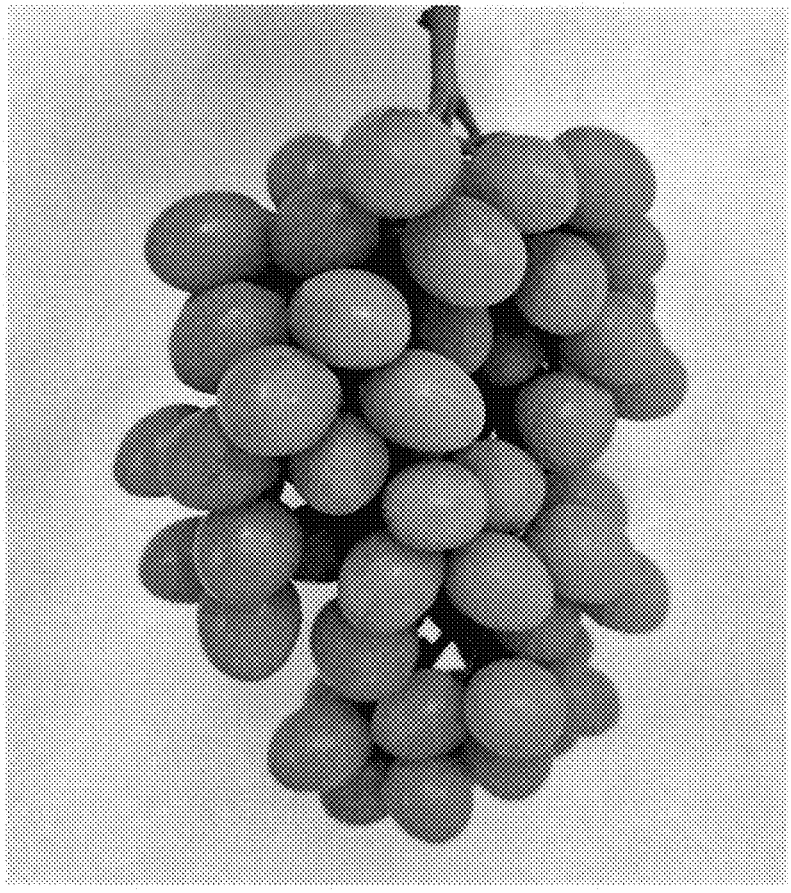
FIG. 2B is a picture zooming on one commercially handled cluster.
Figure 3A:
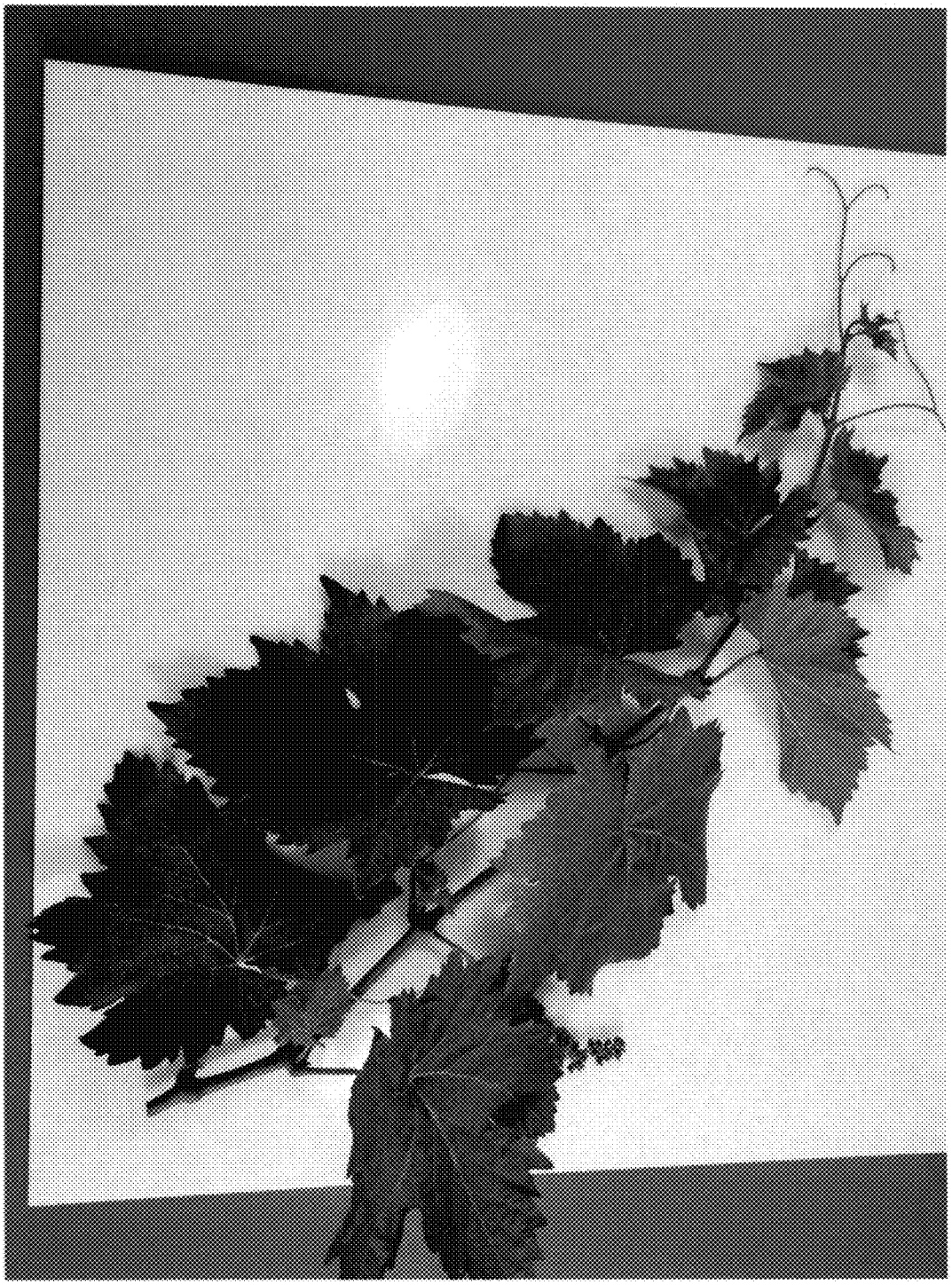
FIG. 3A is a picture of a shoot.
Figure 3B:
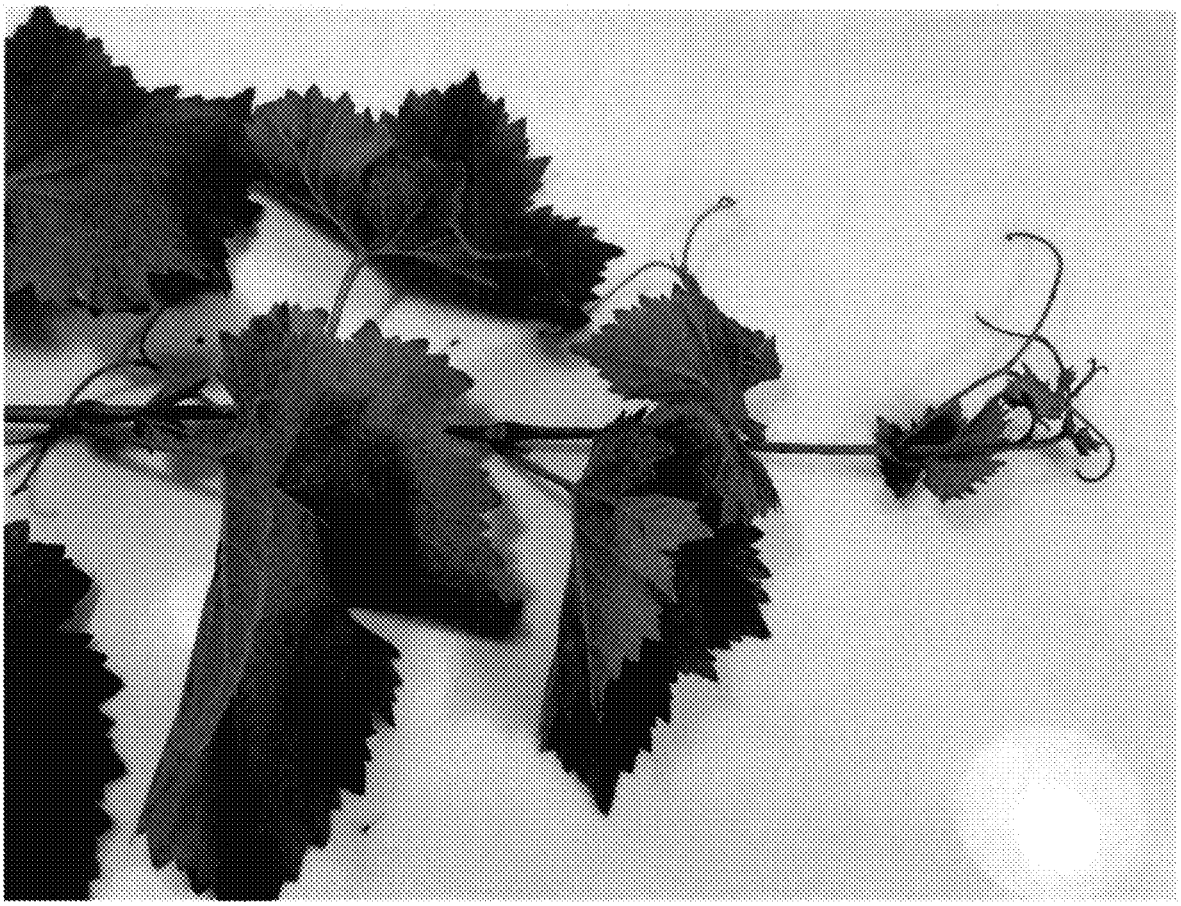
FIG. 3B is a picture zooming at the tip of a shoot.
Figure 4A:
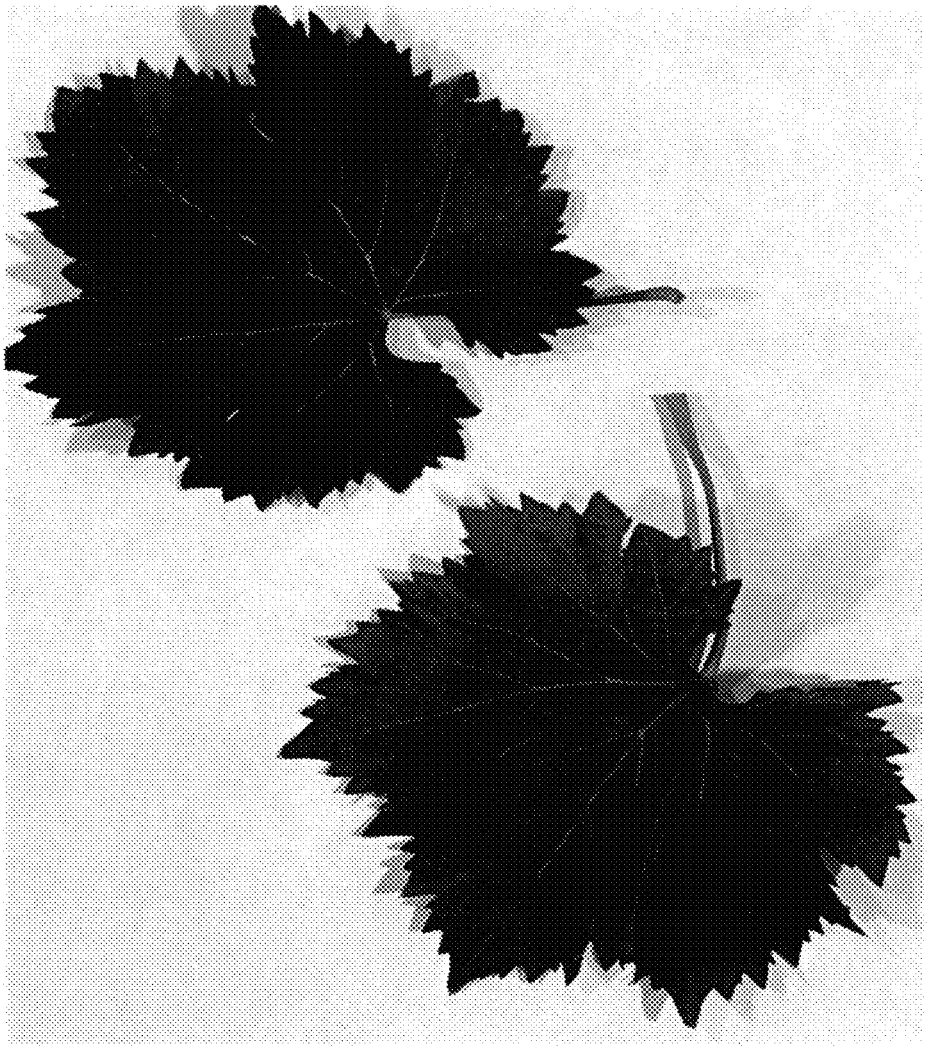
FIG. 4A is a picture of two mature leaves.
Figure 4B:
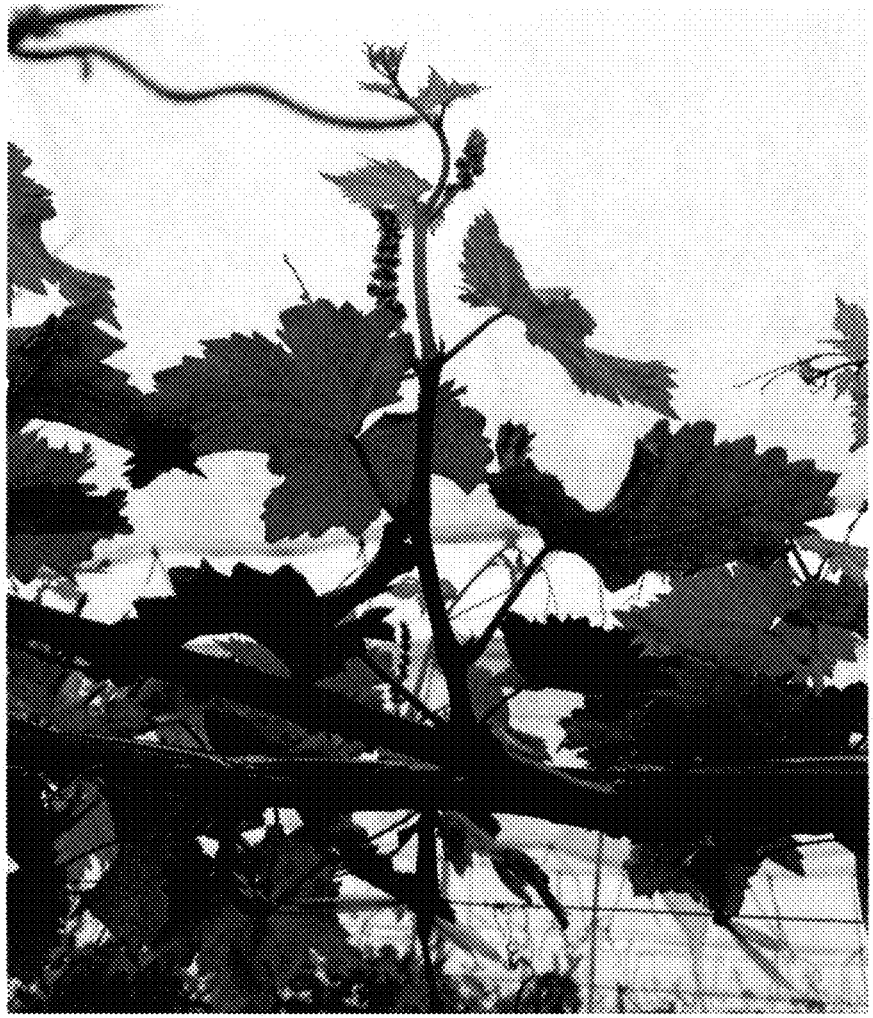
FIG. 4B is a picture of a young shoot in vine.
Figure 5:
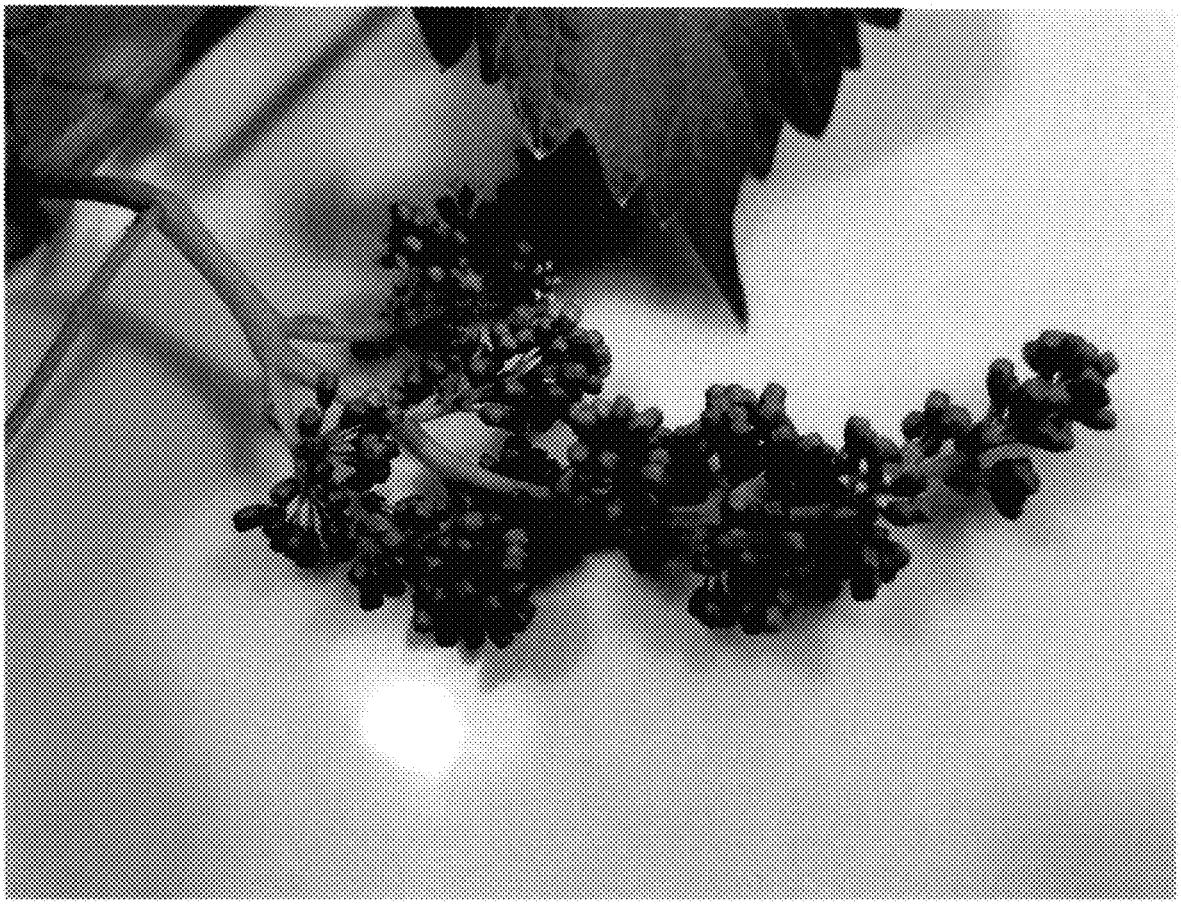
FIG. 5 is a picture of a flowering shoot with flower clusters.
Figure 6:
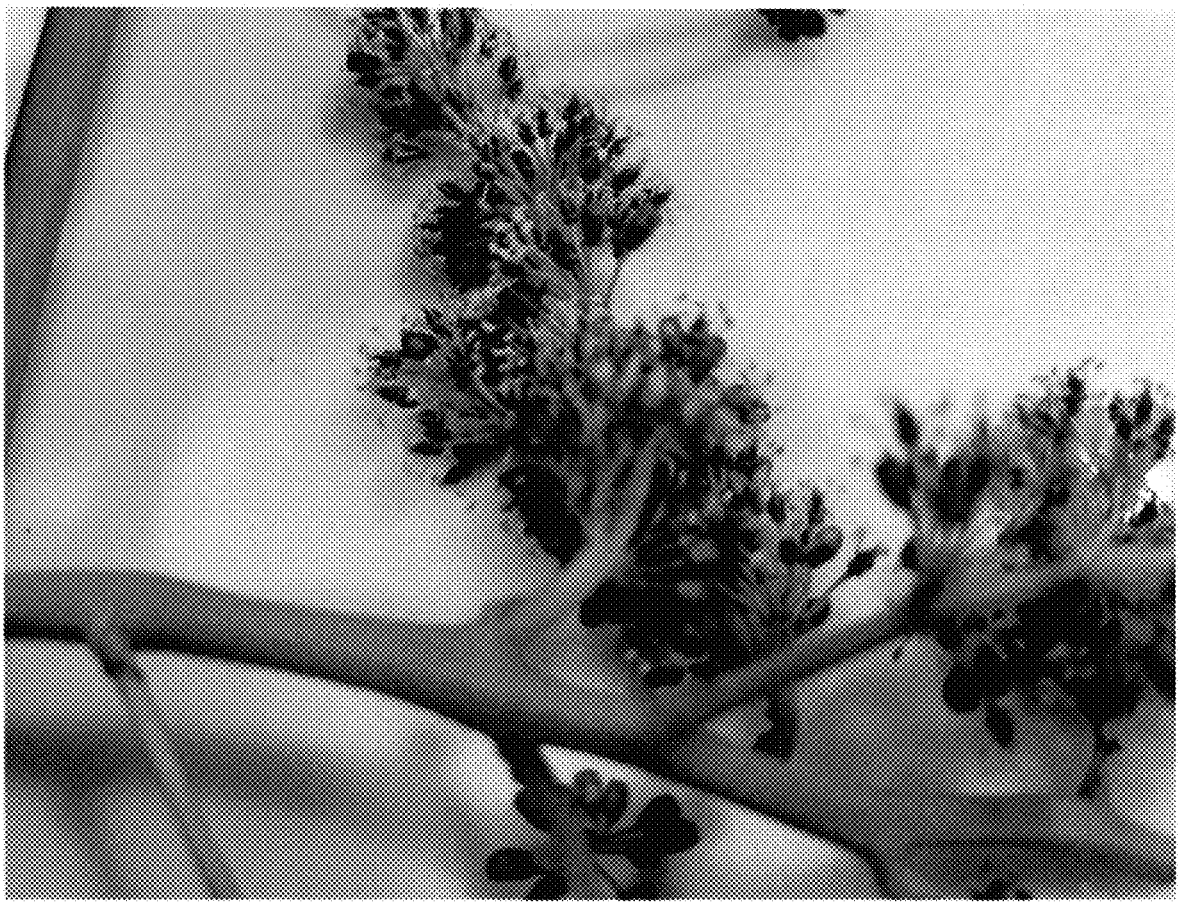
FIG. 6 is a picture zooming at a flower cluster.
Figure 7A:
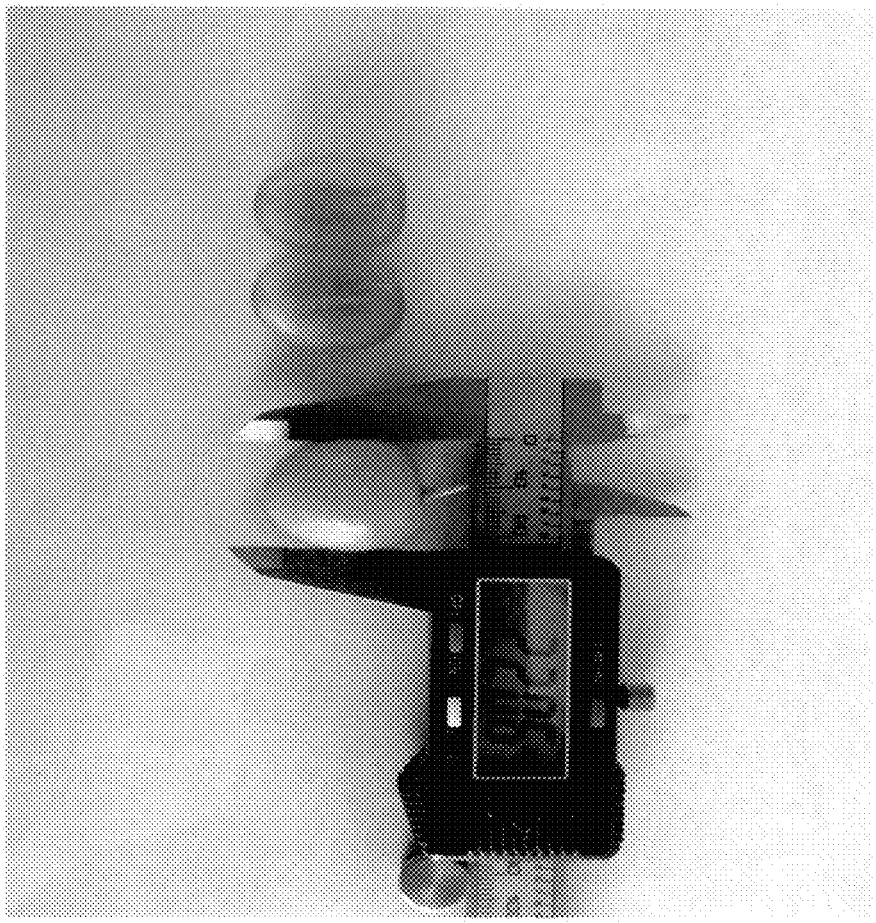
FIG. 7A is a picture oif a berry, showing its size.
Figure 7B:
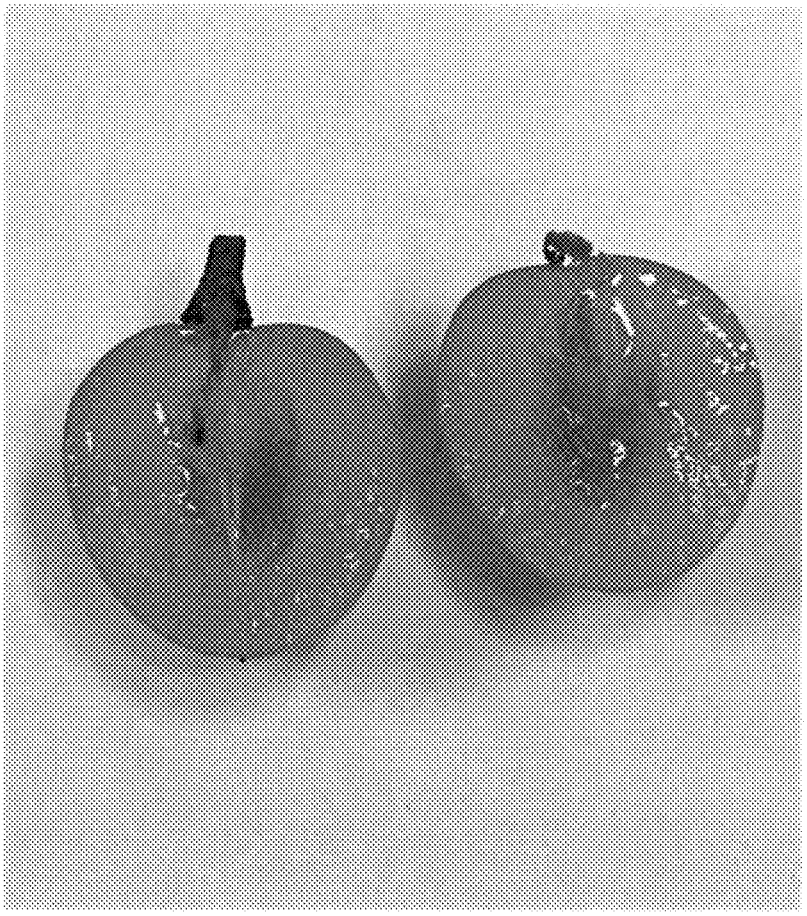
Figure 7C:
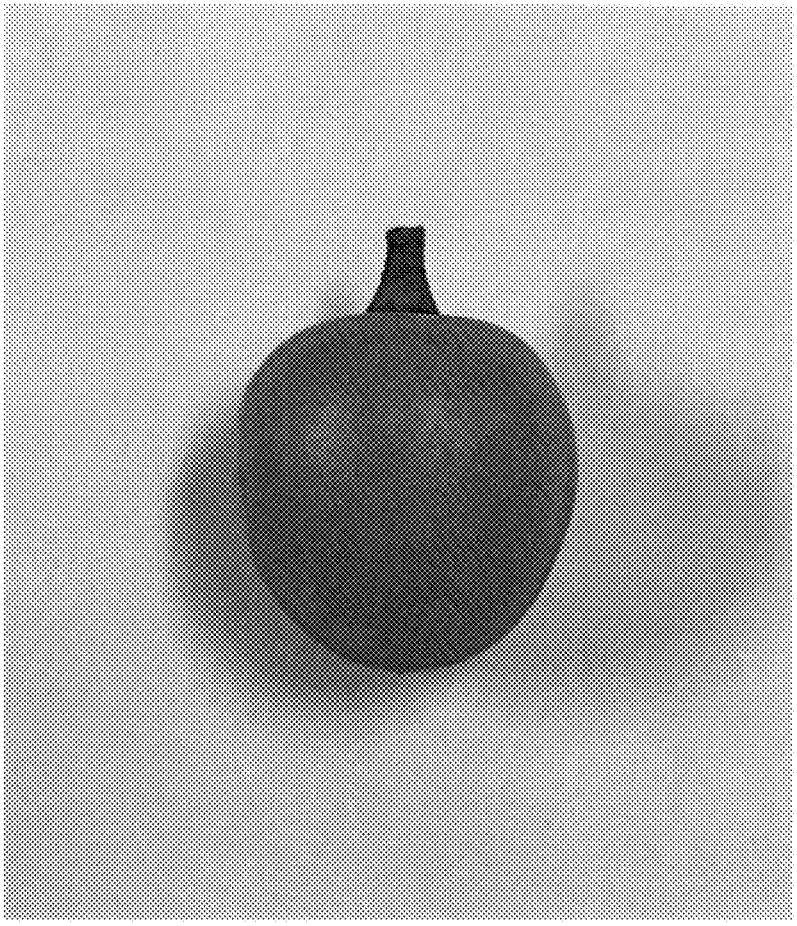
FIG. 7C is a picture of a berry showing its shape.

The following botanical description represents observations on years 2018 to maturity of 2023 from 'INIA-G4' plants located in Vicuña (30°02'15"S;70°41'28"W), Coquimbo Region and La Platina (33°34°22"S 70°37'31"W), Santiago, Central valley of Chile. Plants used for observations were at least three years old. Colors are described using the RHS Colour Chart 6$^{th}$ Edition, published by The Royal Horticultural Society in 2015. Categorical descriptors were taken from the Union for the Protection of New Varieties (UPOV) document TG/50/9. The descriptive data was taken from commercial handled clusters.

LEAVES

Young leaves: 6-8.

*Color of upper surface of first 4 distal unfolded leaves.*—Strong Yellow — green 144A.

*Color of lower surface of first 4 distal unfolded leaves.*—Strong Yellow — green 144B.

*Density of prostrate hairs between veins at upper surface of 4th distal unfolded leaf.*—Absent.

*Density of erect hairs between veins at upper surface of 4th distal unfolded leaf.*—Absent.

*Density of prostrate hairs on veins at lower surface of 4th distal unfolded leaf.*—Absent.

*Density of erect hairs on veins at lower surface of 4th distal unfolded leaf.*—Absent.

Mature leaves: 17-30.

*Color of upper surface.*—Moderate Olive Green 137B and Grayish Olive Green NN137A.

*Color of lower surface.*—Moderate Yellowish Green 138A and Grayish Olive Green NN137D

*Average length.*—About 20 cm.

*Average width.*—About 19 cm.

*Size of blade.*—Large.

*Shape of blade.*—Pentagonal.

*Number of lobes.*—Five.

*Anthocyanin coloration of main veins on the upper side of the blade.*—Absent or very low.

*Mature leaf profile.*—Undulate.

*Blistering surface of blade upper surface.*—Absent or very weak.

*Shape of teeth.*—Mixture of both sides straight and both sides convex.

*Length of teeth.*—Medium (6 mm).

*Width of teeth.*—Medium (7 mm).

*Ratio length/width of teeth.*—Medium (0.86).

*Arrangement of lobes of petiole sinus.*—Half open.

*Tooth at petiole sinus.*—Absent.

*Petiole sinus limited by veins.*—Absent.

*Arrangement of upper lateral sinus.*—Lobes slightly overlapped.

*Depth of upper lateral sinus.*—Shallow.

*Density of prostrate hairs between veins on lower surface of blade.*—Absent or very sparse.

*Density of erect hairs between veins on lower surface of blade.*—Absent or very sparse.

*Density of prostrate hairs on main veins on upper surface of blade.*—Absent or Very sparse.

*Density of erect hairs on main veins on upper surface of blade.*—Absent or very sparse.

FLOWERS

General:

*Flower sex.*—Fully developed stamens and fully developed gynoecium.

*Position of first flowering node.*—Between 4th and 5$^{th}$ node.

*Number of inflorescences per shoot.*—2.

*Date of full bloom.*—Around November 14$^{th}$, Central valley of Chile.

*Duration of bloom period.*—On average, about 7 days.

*Time of bloom.*—Medium, around, November 10$^{th}$, Central valley of Chile.

*Petal number.*—5.

*Petal length.*—1.1 mm.

*Petal width.*—0.8 mm.

*Petal color upper surface.*—Green 143C.

*Petal color lower surface.*—Green 143C.

*Petal upper surface texture.*—Smooth.

*Petal lower surface texture.*—Smooth.

*Filaments color.*—Green Yellow 1D.

*Style length.*—2.1 mm.

*Style color.*—Green 143A.

*Filament length.*—2 mm.

*Filament color.*—Pale greenish yellow 1D.

*Anther color.*—Yellow Green 151D.

*Pollen color.*—Yellow Green 151D.

*Amount of pollen.*—Abundant.

*Cluster size at flowering.*—29 cm.

FRUIT

General:

*Ripening period.*—Mid season. Approximately February 1st in Chile Central Valley.

*Use.*—Fresh market.

*Storage quality.*—Good.

*Shipping quality.*—Good.

*Solids-sugar.*—Refractometer test about 19.0° Brix.

*% Titratable acidity.*—about 0.75%.

*Sugar/acid ratio.*—19/0.75=25.3.

Cluster:

*Cluster size (peduncle excluded).*—Large.

*Mature cluster weight.*—About 700 g.

*Mature cluster length.*—About 17 cm.

*Mature cluster density.*—Lax.

*Number of berries.*—About 90.

*Form.*—Conical.

Peduncle:

*Length of peduncle.*—Short About 3 cm.

*Lignification of peduncle.*—Medium.

*Color.*—Strong Yellow — Green 144A.

Berry:

*Berry size.*—Large.

*Berry shape.*—Ovoid.

*Berry weight.*—About 7.2 g when treated with gibberellic acid.

*Presence of seeds.*—Rudimentary.

*Cross section.*—Circular.

*Dimensions.*—Longitudinal axis (polar diameter) about 28 mm; horizontal axis (equatorial diameter) about 20 mm.

*Skin color (without bloom).*—Yellow-green — Strong yellowish green N144A.

*Flesh color.*—Absent of very weak.

*Juiciness of flesh.*—Slightly Juicy.

*Berry firmness.*—Very firm.

*Particular flavor.*—Sweet.

*Bloom (cuticular wax).*—Medium.

*Berry separation from pedicel.*—Difficult.

*Uniformity of size.*—Uniform.

Skin:

*Thickness.*—Thin.
*Texture.*—Smooth.
*Reticulation.*—Absent.
*Roughness.*—Absent.

VINE

General:

*Size.*—Large. In an overhead trellis system 3 m (between rows)×2.0 m (between vines) the vine is trained to 2.1 m height. The width of the plant is adjusted to the planting distance (3×2 m).
*Vigor.*—Strongly vigorous.
*Density of foliage.*—High.
*Productivity.*—Very productive, about 20 to 24 kg/vine.
*Trunk color.*—Grey brown N199C.
*Trunk texture.*—Rough.
*Rootstock.*—'Harmony' (unpatented).
*Time of bud burst.*—September 26$^{th}$ (early) in Central valley of Chile.

SHOOTS

Young shoot: 2,3,4,5 as per the Grapevine Guidelines from International Union for the Protection of New Varieties of Plants (TG/50/9).

*Form of tip.*—Fully open.
*Intensity of anthocyanin coloration of tip.*—Absent or very weak.
*Density of prostrate hairs on tip.*—Absent or very sparse.
*Density of erect hairs on tip.*—Absent or very sparse.

Flowering shoot:

*Attitude during flowering on shoot which are not tied.*—Erect.
*Color of dorsal side of internodes.*—Strong yellow green 141D and small shades of deep pink 185D.
*Color of ventral side of internodes.*—Strong yellow green 141D.
*Color of dorsal side of node.*—Strong yellowish green 141C.
*Color of ventral side of nodes.*—Strong yellowish green 141C.
*Density of erect hairs on nodes.*—Absent or very sparse.
*Erect hairs on internode.*—Absent or very sparse.
*Density of prostrate hairs on nodes.*—Sparse.
*Density of prostrate hairs internodes.*—Sparse.

Woody shoot:

*Length.*—2.5 m.
*Diameter.*—0.9 cm.
*Internode length.*—Medium, about 8.0 to 11.0 cm.
*Cross section.*—Circular.
*Surface texture.*—Smooth.
*Color.*—Light Reddish brown 177B.

Tendrils:

*Length of tendrils.*—Medium (22 cm).
*Form.*—Trifurcated.
*Number of consecutive tendrils.*—2.

Having thus described and illustrated the new variety of grapevine, I claim:

1. A new and distinct variety of grapevine plant named 'INIA-G4' as illustrated and described.

* * * * *